United States Patent [19]

Foos

[11] Patent Number: 5,322,163

[45] Date of Patent: Jun. 21, 1994

[54] CATHETER TRAY PACKAGE WITH LOCKABLE INSERT

[75] Inventor: Douglas E. Foos, Barrington Hills, Ill.

[73] Assignee: Plastofilm Industries, Inc., Wheaton, Ill.

[21] Appl. No.: 74,139

[22] Filed: Jun. 9, 1993

[51] Int. Cl.⁵ .............................................. B65D 85/08
[52] U.S. Cl. .................................................... 206/364
[58] Field of Search ................................ 206/364, 571

[56] References Cited

U.S. PATENT DOCUMENTS

| | | |
|---|---|---|
| 3,149,747 | 9/1964 | Burgess . |
| 4,005,776 | 2/1977 | Seeley ............................ 206/364 X |
| 4,105,136 | 8/1978 | May ..................................... 220/339 |
| 4,708,245 | 11/1987 | Boeckmann et al. ........... 206/332 X |
| 4,733,778 | 3/1988 | Boeckmann et al. ................ 206/332 |
| 4,779,727 | 10/1988 | Taterka et al. ...................... 206/364 |
| 5,031,775 | 7/1991 | Kane .................................... 206/571 |
| 5,105,942 | 4/1992 | Van Veen et al. ................... 260/364 |
| 5,131,537 | 7/1992 | Gonzales ............................. 206/364 |
| 5,165,540 | 11/1992 | Forney ................................. 206/364 |

FOREIGN PATENT DOCUMENTS 0440427  8/1991  European Pat. Off. .

Primary Examiner—William I. Price
Attorney, Agent, or Firm—Welsh & Katz, Ltd.

[57] ABSTRACT

A catheter tray package includes a tray portion including a floor, an access end, a storage end opposite the access end, and an elongate locking formation secured to the floor and being substantially parallel in relation to a longitudinal axis of the floor. The present package also includes an insert portion configured for sliding engagement with the tray portion and including a planar sheet portion having a catheter access end, a catheter storage end opposite the access end and an elongate keyway formation disposed on the sheet portion for engaging the locking formation to limit the sliding action of the insert portion relative to the tray portion in a first direction, while permitting the insert to be released from engagement with the locking formation in a second direction.

18 Claims, 1 Drawing Sheet

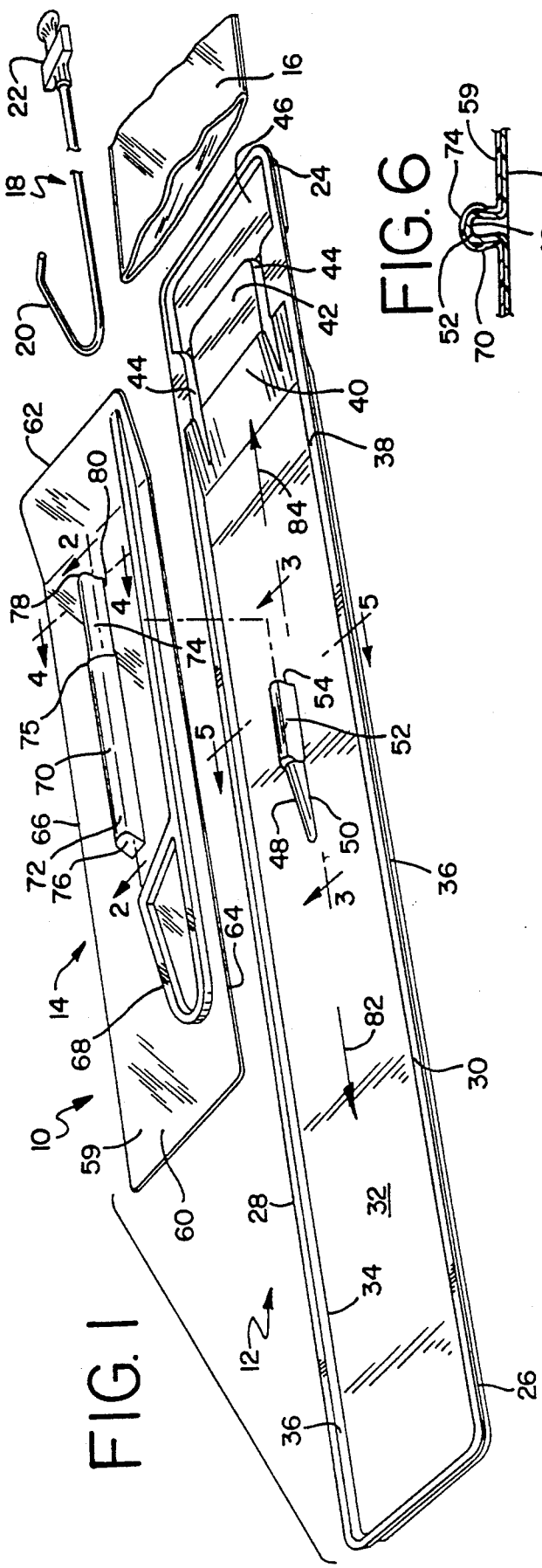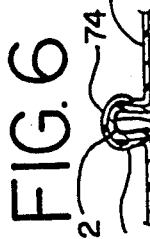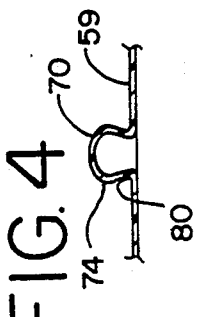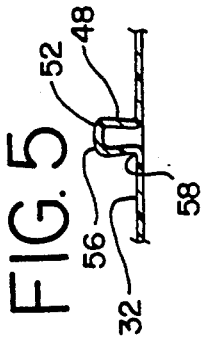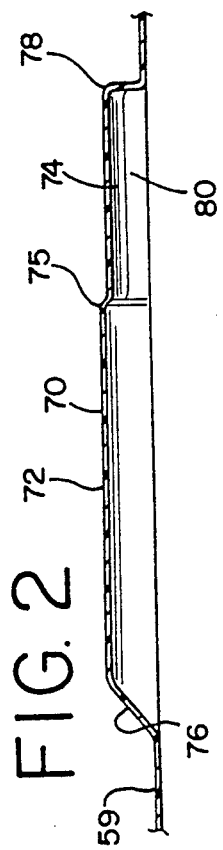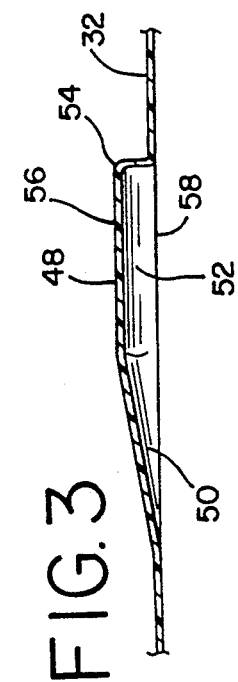

CATHETER TRAY PACKAGE WITH LOCKABLE INSERT

BACKGROUND OF THE INVENTION

The present invention relates generally to packages for medical catheters, and specifically to such a package having a tray portion and an insert portion, wherein the insert portion is releasably lockable in relation to the tray portion.

Conventional medical procedures include an extensive use of flexible catheters for diagnosis as well as various types of treatment. Typical catheters include tip portions having curved configurations designed for passage into and through body passageways such as blood vessels, heart passageways, intestinal lumens and in other regions, in many cases employing ultrasonic or fluoroscopic guidance. Opposite the tip portion is a hub or luer fitting for connection to other catheter manipulation and control devices. Surgeons and other medical personnel have come to rely upon catheter tip portions having specially designed shapes, and it is critical that during packaging and shipment, these shapes be maintained in their initially manufactured and sterilized form.

Another design criterion for catheter packages is that catheter tips are particularly prone to disfigurement during the removal of the catheter from the package. Accordingly, catheter package design efforts have been focused on preventing damage to the catheter tip, either during insertion into, storage within, or removal from the package.

A widely used form of catheter package includes an elongate catheter tray which supports the entire length of the catheter in an immobilized condition, and includes an insert which is slidable relative to the tray. The insert has a recess formed to enclose and protect the curved catheter tip.

The combined tray, insert and catheter combination is placed in a sealed flexible pouch to maintain sterile conditions. To remove the catheter from the package, the pouch is opened and the rear or access end of the catheter is pulled relative to the tray, which causes the insert and the catheter tip to move toward the access end of the tray. At a certain point, the insert separates from the tray, allowing the removal of the catheter tip. Often, such tray packages include ramps or other integral formations for facilitating the separation of the insert from the tray portion upon opening of the package.

A disadvantage of conventional catheter trays is that the tray portion, which is often produced by thermoforming sheets of polymeric material, is provided with side edge rails having undercuts defining a track in which the insert slides. These tracks are used both to retain the insert in position during shipment to avoid damaging the catheter tip, and also provide a guide for the withdrawal of the insert when the package is opened. However, it has been found that this type of undercut side edge configuration is difficult to accurately and efficiently die cut.

Another concern of users of conventional catheter tray packages is that the insert be immobilized on the tray during shipment, and until the package is opened. Tray packages employing undercut side edges also must be provided with some sort of locking or friction fit formation to secure the insert in position. These additional locking formations, whether found on the tray or on the insert, create problems in tool design and package formation techniques.

Accordingly, it is an object of the present invention to provide a catheter tray package having an insert tray retaining and guide configuration which is effective in releasably locking the insert in position relative to the tray portion without the use of undercut formations.

It is another object of the present invention to provide a catheter tray package with an insert locking configuration which easily releases upon the pulling of the luer end of the catheter by medical personnel when the package is opened.

Still another object of the present invention is to provide a catheter tray package in which the locking formation also is configured to facilitate the separation of the insert portion from the tray portion upon the opening of the package.

SUMMARY OF THE INVENTION

The above-identified objects are met or exceeded by the present catheter tray package, which includes a tray portion and an insert portion, and is preferably enclosed by a flexible pouch. The tray portion is provided with a generally centrally located locking formation, which engages a keyway formation on the insert portion to immobilize the insert on the tray prior to the opening of the package.

More specifically, the present catheter package includes a tray portion including a floor, an access end, a storage end opposite the access end, and an elongate locking formation secured to the floor and being substantially parallel in relation to a longitudinal axis of the floor. The present package also includes an insert portion configured for sliding engagement with the tray portion and including a planar sheet portion having a catheter access end and a catheter storage end opposite the access end. An elongate keyway formation is disposed on the sheet portion for engaging the locking formation to limit the sliding action of the insert portion relative to the tray portion in a first direction, while permitting the insert to be released from engagement with the locking formation in a second direction.

BRIEF DESCRIPTION OF THE DRAWING

FIG. 1 is an exploded top perspective elevational view of the present catheter tray package;

FIG. 2 is a sectional view taken along the line 2—2 of FIG. 1 and in the direction indicated generally;

FIG. 3 is a sectional view taken along the line 3—3 of FIG. 1 and in the direction indicated generally;

FIG. 4 is a sectional view taken along the line 4—4 of FIG. 1 and in the direction indicated generally;

FIG. 5 is a sectional view taken along the line 5—5 of FIG. 1 and in the direction indicated generally; and FIG. 6 is a sectional view showing the insert and tray portions of the present package in engaged relationship, and is a combination of the views of FIGS. 4 and 5.

DESCRIPTION OF THE PREFERRED EMBODIMENT

Referring now to FIG. 1, the present catheter tray package is generally designated 10, and includes two major components, a tray portion, generally designated 12, and an insert portion, generally designated 14. A flexible pouch or bag 16 is preferred for maintaining sterility. The pouch 16 is dimensioned to enclose the tray portion 12 and the insert portion 14 with a catheter disposed therein.

A catheter of the type intended to be contained within the present package 10 is generally designated 18, and includes a tip section 20 and a hub or luer fitting 22 located opposite the tip section. The tip section 20 is provided in a particular shape, depending on the medical function or procedure to be performed by the catheter 18, and it is an important goal of the present package 10 to maintain and protect the shape of this tip section. The hub 22 is constructed and arranged to be connected to other catheter control devices (not shown) as are known in the art.

The tray portion 12 has an access end 24, a catheter tip storage end 26 opposite the access end, a first side 28 and a second side 30. A generally planar floor 32 has a peripheral edge 34 to which is integrally joined a sidewall 36. The sidewall 36 projects generally perpendicularly or normally relative to the floor 32 and is provided with a laterally outwardly extending lip 38.

At or near the access end 24, the tray portion 12 is provided with a ramp 40 which is inclined to connect the floor 32 with a transversely positioned support platform 42. At least one and preferably two catheter grooves 44 are formed in the platform 42 for accommodating the catheter 18. The support platform 42 defines a hub pocket 46 between the platform and the access end 24, the pocket being dimensioned to accommodate the hub portion 22 of the catheter 18.

The tray 12 is preferably thermoformed from a sheet of polymeric material, such as polyvinylchloride, high impact styrene or other similar material, following which the tray is die cut from the sheet as is well known in the art. It is contemplated the tray 12 may also be manufactured using other conventional molding techniques, such as injection molding.

Referring now to FIGS. 1, 3 and 5, an elongate locking formation 48 is secured to the floor 32 and is substantially parallel to a longitudinal axis of the floor, as well as to the first and second sides 28, 30. In the preferred embodiment, the formation 48 is integrally formed with the tray portion 12 and is generally centrally located on the floor 32 between the first and second sides 28, 30. The elongate locking formation 48 has a first portion 50 corresponding to the storage end 26 of the tray portion 12, and a second portion 52 corresponding to the access end 24. The first portion 50 also has a generally inclined configuration which slopes downward toward the storage end 26.

In cross-section, the locking formation 48, and particularly the second portion 52 has a generally inverted "U" shape with a generally radiused or rounded, truncated end 54. The second portion 52 has an upper portion 56, and a lower edge 58 where the formation meets the floor 32. In cross-section, the first and second portions 50, 52 each have a width, the width of the second portion 52 being generally greater than the width of the first portion 50. In addition, the cross-sectional width between the lower edges 58 is narrower than the width of the upper portion 56.

Referring now to FIGS. 1, 2 and 4, the insert portion 14 includes a sheet portion 59 of preferably transparent thermoformable material, with a catheter tip storage end 60 which corresponds to the tip storage end 26 of the tray portion 12. Opposite the tip storage end 60 is a catheter access end 62 which corresponds to the access end 24 of the tray portion 12. It will be seen that the insert portion 14 is relatively shorter than the tray portion 12. An advantage of the present package 10 is that a single tray portion 12 may be used with a variety of insert portions 14, each formed to be specific for a certain type and/or length of catheter tip.

Insert portion 14 also has generally parallel first and second sides 64, 66 which slidingly engage the sidewalls 36 of the tray portion 12. A catheter tip recess 68 is integrally formed in the insert portion 14 and is configured to securely retain the catheter tip 20. In the preferred embodiment, the access end 62 is inclined upwardly in a plane generally parallel with a plane defined by the ramp 40 on the tray portion 12. However, the inclination of the access end 62 is variable depending on the application.

Also included on the insert portion 14 is an elongate keyway formation 70 located on the sheet portion 59 and configured to engage the locking formation 48 on the tray portion 12. The engagement of the keyway formation 70 on the locking formation 48 limits the sliding action of the insert portion 14 relative to the tray portion 12 in a direction toward the catheter storage end 26. At the same time, the engagement of the keyway formation 70 on the locking formation permits the insert portion 14 to be released from engagement with the locking formation in a direction towards the catheter access end 24.

More specifically, referring to FIGS. 1, 2, 4, and 6, the keyway formation 70 is configured to tightly accommodate a corresponding portion of the locking formation 48. Accordingly, the elongate keyway formation 70 has a rear portion 72 corresponding to the catheter storage end 26 of the tray portion 12, and a front portion 74 corresponding to the catheter access end 24. A shoulder 75 defines the front and rear portions 72, 74. In similar fashion to the locking formation 48, the rear and front portions 72, 74 of the keyway formation generally define an inverted "U"-shaped configuration. Furthermore, in the preferred embodiment, the rear portion 72 of the keyway formation 70 has an end 76 which is ramped or inclined, while the front portion 74 has an end 78 which is truncated and radiused or rounded to accommodate the truncated end 54 of the locking formation 48.

For proper operation of the present catheter tray, the rear portion 72 of the keyway formation 70 has a cross-sectional width which is generally wider than the width of the front portion 74. Also, the front portion 74 of the keyway formation 70 has a lower edge 80 which is narrower in cross-sectional width than the upper portion of the formation to provide a tight fit between the keyway formation 70 and the locking formation 48. Upon engagement of the insert portion 14 with the locking formation 48 of the tray portion 12, a tight yet releasable friction fit exists between the respective front portion 74 of the keyway portion and the second portion 52 of the locking formation 48 (best seen in FIG. 6).

In order to preserve sterile conditions of the catheter 18, the package 10 is provided with the sealing pouch 16. The pouch 16 is dimensioned to sealingly enclose the tray portion 12, the insert portion 14, and a catheter 18 located therein. In the preferred embodiment, the pouch 16 is fabricated of transparent, heat sealable plastic film, however other conventional sealing or wrapping materials are contemplated.

In operation, the present catheter package 10 is assembled by placing the catheter tip 20 into the catheter tip recess 68 of the insert portion 14. The insert portion 14 is then placed upon the tray portion 12 so that the rear portion 72 of the keyway formation 70 engages the locking formation 48. The insert 14 is then slid longitudinally relative to the tray portion 12 in the direction indicated by the arrow 82, which points toward the catheter storage end 26.

Once the radiused end 78 of the front portion 74 contacts the truncated end 54 of the locking formation 48, further movement of the insert portion 14 in the direction 82 is prevented, since the locking formation 48 acts as a stop for the insert portion 14. The locking engagement of the keyway formation 70 upon the locking formation 48 also prevents the insert from moving laterally during shipping. In fact, when the present package 10 is in the locked position, the catheter tip 20 is virtually immovable, and the insert portion 14 will not disengage from the tray portion 12 even if the package 10 is dropped, unless the package itself is broken.

The packaging of the catheter 18 is completed by the insertion of the hub 22 into the hub pocket 46, and the catheter is also placed in one of the grooves 44. If desired, the grooves 44 are constructed to retain the catheter 18 by a friction-type snap fit. Next, the pouch 16 is placed over the assembled tray portion 12, the insert portion 14 and the catheter 18, and is sealed with heat or in an equivalent manner well known to skilled practitioners.

When a medical technician or physician desires to open the catheter package 10, initially, the pouch 16 is broken and removed, and the user then pulls the catheter hub 22 in the direction indicated by the arrow 84, which points toward the catheter access end 24, and which is in the opposite direction to the arrow 82. In response to a force exerted in the direction 84, the insert portion is pulled towards the catheter access end 24, and the keyway formation 70 becomes disengaged from the locking arrangement with the locking formation 48. However, the formation 48 still serves as a guide for the movement of the insert portion 14 towards the catheter access end 24. In addition, the sidewalls 36 also guide the travel of the insert portion 14 to prevent damage to the catheter tip 20. An advantage of the construction of the present package 10 is the proper guiding and locking of the insert portion 14 relative to the tray portion 12 without the use of undercut formations.

As the hub 22 is pulled further, the end 76 of the rear portion 72 of the keyway formation 70 engages the inclined first portion 50 of the locking formation 48, which separates the insert portion 14 from the tray portion 12. Next, the ramped access end 62 of the insert portion 14 engages the ramp 40 on the tray portion 12 and is forced upward. Thus, the insert portion 14 is forced upward and disengages from the tray portion 12 upon the exertion of sufficient pulling force in the direction designated by the arrow 84. During this process, the catheter tip 20 remains in the catheter tip recess 68 until the insert portion 14 is totally disengaged from the tray portion 12. The catheter 18 may then be removed from the insert portion 14.

While a particular embodiment of the catheter tray package with lockable insert of the invention has been shown and described, it will be appreciated by those skilled in the art that changes and modifications may be made thereto without departing from the invention in its broader aspects and as set forth in the following claims.

What is claimed is:

1. A catheter package, comprising:

a tray portion including a floor, an access end and a storage end opposite said access end;

an elongate locking formation secured to said floor and being substantially parallel in relation to a longitudinal axis of said floor;

an insert portion configured for sliding engagement with said tray portion and including a planar sheet portion having a catheter access end, and a catheter storage end opposite said access end;

an elongate keyway formation disposed on said sheet portion for engaging said locking formation to limit the sliding action of said insert portion relative to said tray portion in a first direction, while permitting said insert to be released from engagement from said locking formation in a second direction.

2. The package as defined in claim 1 wherein said tray portion further includes first and second sidewalls disposed generally normally to said floor.

3. The package as defined in claim 1 wherein said tray portion also includes a ramp formation proximate said access end.

4. The package as defined in claim 1 wherein said elongate locking formation is integrally formed into said floor and is substantially centrally located thereon between first and second side edges of said tray portion.

5. The package as defined in claim 1 wherein said elongate locking formation has a first portion corresponding to said storage end, and a second portion corresponding to said access end, said first portion having a generally inclined configuration.

6. The package as defined in claim 5 wherein said second portion has a generally inverted "U" shape in cross-section, with a generally radiused, truncated end.

7. The package as defined in claim 6 wherein said second portion has an upper portion, and a lower edge where said formation meets said floor, said lower edge being generally narrower in width than said upper portion.

8. The package as defined in claim 1 wherein said elongate keyway formation has a rear portion corresponding to said storage end of said tray portion and a front portion corresponding to said access end of said tray portion, said front and rear portions generally defining an inverted "U"-shaped configuration.

9. The package as defined in claim 8 wherein said front and rear portions each have a width, said width of said rear portion being generally greater than said width of said front portion.

10. The package as defined in claim 9 wherein said rear portion has an end with a ramped configuration.

11. The package as defined in claim 1 wherein said keyway formation is configured to tightly accommodate a corresponding portion of said locking formation.

12. The package of claim 1 further including a flexible pouch dimensioned to sealingly enclose said tray portion and said insert portion with a catheter located therein.

13. A catheter package, comprising:

a tray portion including a floor, an access end, a storage end opposite said access end and a ramp proximate to said access end;

an elongate locking formation secured to said floor and being substantially parallel in relation to a longitudinal axis of said floor;

an insert portion configured for sliding engagement with said tray portion and including a planar sheet portion having a catheter access end, a catheter tip recess and a catheter storage end opposite said access end;

an elongate keyway formation disposed on said sheet portion for engaging said locking formation to limit the sliding action of said insert portion relative to said tray portion in a direction toward said catheter storage end, while permitting said insert to be released from engagement from said locking formation when pulled in a direction toward said catheter access end.

14. The package as defined in claim 13 wherein said elongate locking formation has a first portion corresponding to said storage end, and a second portion corresponding to said access end, said first portion having a generally inclined configuration.

15. The package as defined in claim 14 wherein said second end has a generally inverted "U" shape in cross-section, with a generally radiused, truncated end.

16. The package as defined in claim 15 wherein said second end has an upper portion, and a lower edge where said formation meets said floor, said lower edge being generally narrower in width than said upper portion.

17. The package as defined in claim 13 wherein said elongate keyway formation has a rear portion corresponding to said storage end of said tray portion and a front portion corresponding to said access end of said tray portion, said front and rear portions generally defining an inverted "U"-shaped configuration.

18. The package as defined in claim 17 wherein said front and rear portions each have a width, said width of said rear portion being generally greater than said width of said front portion.

* * * * *